United States Patent [19]

Pelmulder et al.

[11] Patent Number: 4,712,583

[45] Date of Patent: Dec. 15, 1987

[54] PRECISION PASSIVE FLAT-TOP VALVE FOR MEDICATION INFUSION SYSTEM

[75] Inventors: John P. Pelmulder, Chatsworth; Lanny A. Gorton, Sunland; Armen J. Guleserian, Simi Valley; John H. Livingston, Santa Monica, all of Calif.

[73] Assignee: Pacesetter Infusion, Ltd., Sylmar, Calif.

[21] Appl. No.: 867,824

[22] Filed: May 27, 1986

[51] Int. Cl.$^4$ .............................................. F16K 15/14
[52] U.S. Cl. .................................. 137/852; 137/859; 137/494; 604/247
[58] Field of Search ............... 137/859, 843, 845, 846, 137/847, 851, 852, 855, 494; 604/247

[56] References Cited

U.S. PATENT DOCUMENTS

| | | | |
|---|---|---|---|
| 2,467,189 | 2/1949 | Hess | 137/496 |
| 2,497,906 | 2/1950 | Peters et al. | 137/859 |
| 2,758,609 | 8/1956 | Dickert et al. | 137/859 |
| 3,190,496 | 6/1965 | Weiland, Jr. et al. | 137/859 |
| 4,143,853 | 3/1979 | Abramson | 137/846 |
| 4,355,639 | 10/1982 | DiSalvo | 137/859 |
| 4,493,339 | 1/1985 | Porter, Jr. | 137/859 |

*Primary Examiner*—Harold W. Weakley
*Attorney, Agent, or Firm*—Leslie S. Miller

[57] ABSTRACT

A valve for use in medical applications is disclosed which is a highly precise, passive, one-way valve which makes an excellent inlet valve or outlet valve in a drug infusion pump. The valve operates with a very small forward pressure, requires only a small amount of fluid in the valve chamber, and operates in a positive and predictable fashion, even after an extended shelf life. The valve, may be inexpensively molded in one piece, thereby facilitating construction of a disposable pump, and may be installed with the portion of the pump housing contacting the top surface of the valve being flat, thereby further reducing manufacturing costs.

17 Claims, 8 Drawing Figures

PRECISION PASSIVE FLAT-TOP VALVE FOR MEDICATION INFUSION SYSTEM

BACKGROUND OF THE INVENTION

Field of the Invention

The present invention relates generally to a small, precision, passive one-way valve for medical applications which opens when a minimal pressure drop occurs across the valve, and more particularly to an improved valve for use in a medical infusion pump, which improved valve may be installed in a flat-top configuration allowing the portion of the housing on top of the valve to be flat rather than precision contoured, thereby allowing substantial reduction in the cost of the pump.

In the past there have been two techniques used to deliver drugs which may not be orally ingested to a patient. The first such technique is through an injection, or shot, which delivers a large dosage at relatively infrequent intervals to the patient. This technique is not always satisfactory, particularly when the drug being administered is lethal or has negative side effects when delivered in a large dosage. This problem results in smaller injections being given at more frequent intervals.

Alternatively, the second technique involves administering a continuous flow of medication to the patient through an IV bottle. Medication may also be delivered through an IV system with an injection being made into a complex maze of IV tubes, hoses, and other paraphernalia. As an alternative to these two techniques of administering medication to a patient, the recent addition of medication infusion pumps has come as a welcome improvement.

Infusion pumps are utilized to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained precisely by operating on a continuous time basis.

One of the essential elements of an infusion pump is a one-way valve, one or more of which is required in virtually any design for an infusion pump. Such a valve must be highly precise, operating in a passive manner to open with a relatively small break pressure or cracking pressure in the desired direction of flow through the valve. The valve must also be resistant to a substantially higher reverse pressure, not opening or leaking at all, since any reverse flow in the opposite direction would result a reduction in the amount of medication being delivered, and an imprecise infusion pump which would be totally unacceptable.

The valve must be easily manufactured, and must have both an extended shelf life and a long operating life. It must also be made from a material which is of a medical grade, and which will not be affected by any of the numerous medications which may be administered by the infusion pump.

An additional requirement has been imposed by the important design consideration of disposability. It is desirable that the pump portion of the infusion pump device be disposable, and therefore the valve must in addition to all the requirements previously mentioned be inexpensive, and must also be installable in the pump easily. Since the inexpensive nature of the disposable pump mandates against expensive molding techniques, it is a primary object of the valve that it be installable in the pump with only one half of the housing containing the valve requiring a complex form. More specifically, the top or inlet portion of the housing will be flat save for an opening through which the medication being pumped may flow into contact with and through the valve.

It is also necessary in order to minimize the number of parts required and therefore the cost of construction of the disposable pump that sealing means be included in the integral design of the pump. When the two portions of the pump housing are assembled with the valve therebetween, fluid will be able to flow only through the valve, and not around it. In addition, leaks from the pump between the two portions of the housing will be prevented by the sealing means.

SUMMARY OF THE INVENTION

The disadvantages and limitations of the background art discussed above are overcome by the present invention. With this invention, an inexpensive valve of unitary construction having sealing means integrally included is taught which may be installed between two housing portions, one of which is essentially flat with an aperture therein from which fluid flows into contact with and through the valve.

The valve is molded in unitary fashion of a medical grade elastomer such as silicone rubber. A circular valve disk has on the top side thereof a protruding cylindrical dynamic sealing ridge, which is the actual valve element. A static seal ring having a larger inner diameter than the outer diameter of the valve disc is located concentrically around the valve disk. The valve disk is supported from the static seal ring by a thin support web extending between the static support ring and the valve disk, which web has a plurality of holes therethrough to allow fluid passage.

The valve is installed by locating it in a first housing portion which has provision for receiving the static seal ring, and also includes a web support structure for supporting portion of the web adjacent to the static seal ring. The first housing portion has an aperture therein to allow fluid passing through the valve to exit, which aperture is located on the underside of the valve when it is installed in the first housing portion as described above.

A second housing portion is then installed on top of the valve as previously installed in the first housing portion. The second housing portion, which rests on top of the valve, is essentially flat, and has an aperture therein through which fluid may enter toward the valve. This aperture is located above the valve disk and concentrically within the dynamic sealing ridge. When the second housing portion is installed onto the first housing portion with the valve therebetween, the static seal ring is compressed to create a good seal.

In operation, when the pressure is greater on top of the valve disk than under the valve disk, the valve will tend to open, requiring only a small pressure to operate. However, when this small break pressure is not present, or when a reverse pressure is present, the valve will remain in a closed position. It may thereby be appreciated that the valve has a very positive sealing action when closed, and that it will open easily when the small break pressure (or a greater pressure in that direction) is present.

It is apparent that the valve as described herein may be simply constructed in a single molding operation in one piece, thereby minimizing both parts and costs. The valve may be molded of a medical grade elastomer, which is acceptable for use in an infusion pump, as well as having excellent shelf life and operating life characteristics.

As a result of the novel design of the valve, the portion of the housing mounted on the top side of the valve may be flat, and therefore of economical construction. Even so, an excellent seal is obtained, thereby preventing both leaks out of the pump and in either direction around the valve. Since the valve is highly precise and has only a small required break pressure to open it, it offers excellent operating characteristics. Finally, the economic construction of the valve and the resulting enablement of economic construction of the pump make the valve a valuable addition to the art, particularly for the construction of a disposable pump.

DESCRIPTION OF THE DRAWINGS

These and other advantages of the present invention are best understood with reference to the drawings, in which.

DETAILED DESCRIPTION OF THE PREFERRED EMBODIMENT

Figure 6:
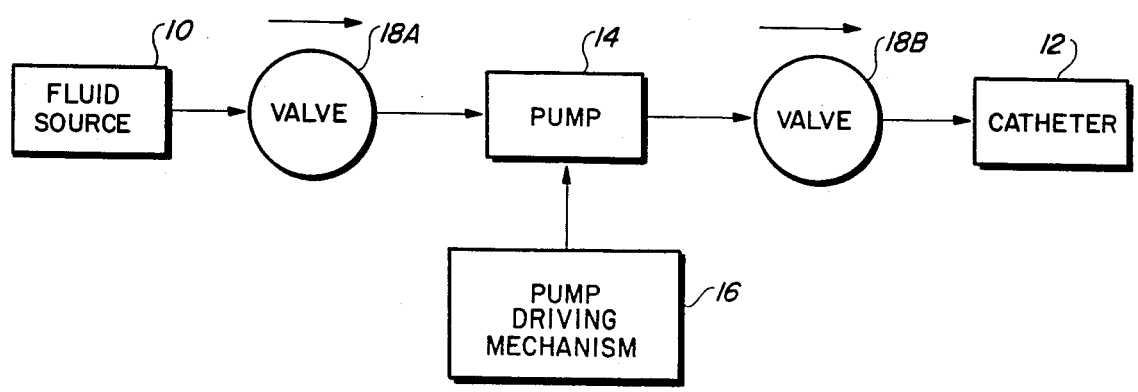
FIG. 6 is a schematic block diagram of the operation of a pump using two of the valves of the present invention.

A possible configuration for an infusion pump using two of the valves of the present invention is illustrated schematically in FIG. 6. Medication contained in a fluid source 10 is to be provided to a patient via a catheter 12, which is of standard design and well known in the art. The fluid driver may be generically described as a pump 14, which may be any of a number of different arrangements, the most common of which is a variable displacement piston and cylinder arrangement.

The pump 14 is driven by a pump driving mechanism 16, which may also be any of a number of different arrangements which are known for controlling an infusion pump. Two one-way valves 18A, 18B are used to control the pumping force generated by the pump 14. The first one-way valve 18A is located in the fluid path between the fluid source 10 and the pump 14, and will only allow fluid to pass from the fluid source 10 to the pump 14. The second one-way valve 18B is located between the pump 14 and the catheter 12, and will only allow fluid to pass from the pump 14 to the catheter 12.

When the displacement of the pump 14 is increasing, fluid will be drawn into the pump 14. Since the second valve 18B will not allow fluid to flow into the pump 14, fluid will be drawn from the fluid source 10 through the first valve 18A into the pump 14. Likewise, when the displacement of the pump 14 is decreasing, fluid will be forced out from the pump 14. Since the first valve 18A will not allow fluid to flow out from the pump 14, fluid will be forced out from the pump 14 through the second valve 18B into the catheter.

For a disposable pump, the two valves 18A and 18B, and the pump 14 would be the disposable components (presumably together with the associated tubing, the catheter, and the empty fluid source). The present invention focuses on the construction of the valves 18A and 18B, which are usually identical. It will be appreciated by one skilled in the art that the present invention may be adapted to have application in virtually any infusion pump conceivable.

Figure 1:
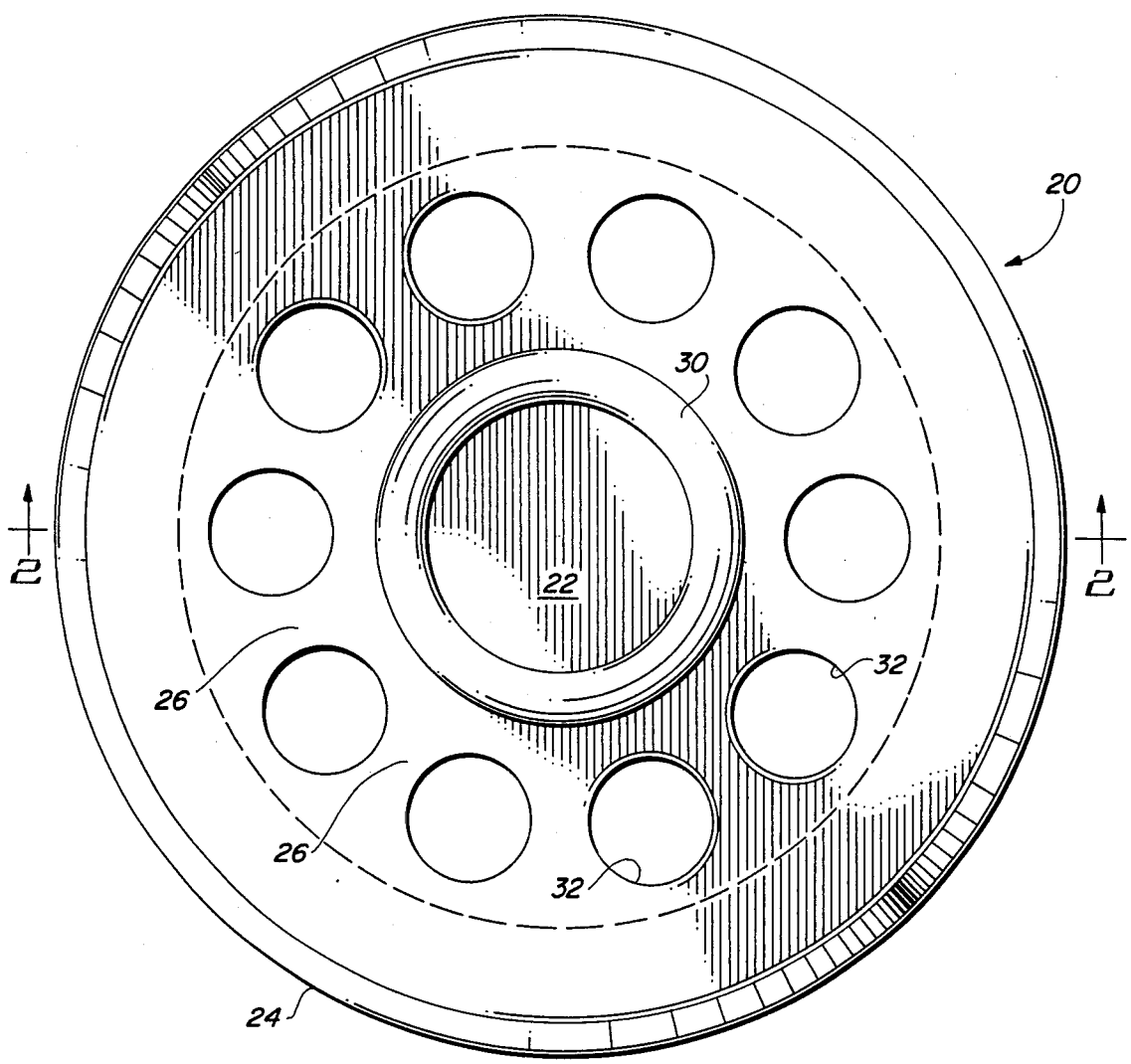
FIG. 1 is a plan view of the top side of the valve of the present invention.
Figure 2:
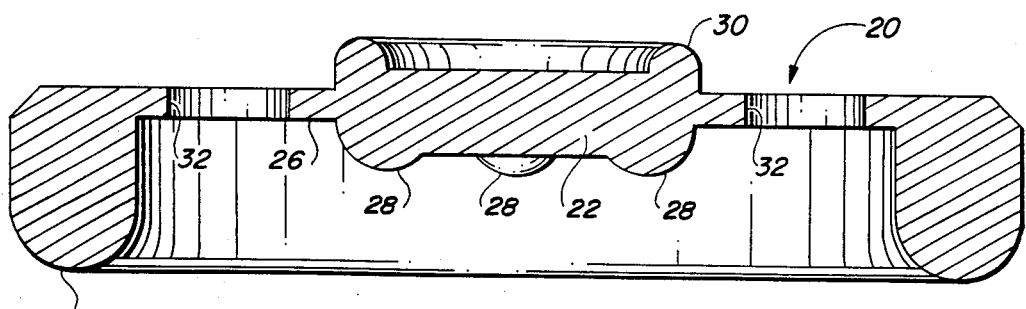
FIG. 2 is a cross-sectional view of the valve of FIG. 1 illustrating the configuration of the valve.
Figure 3:
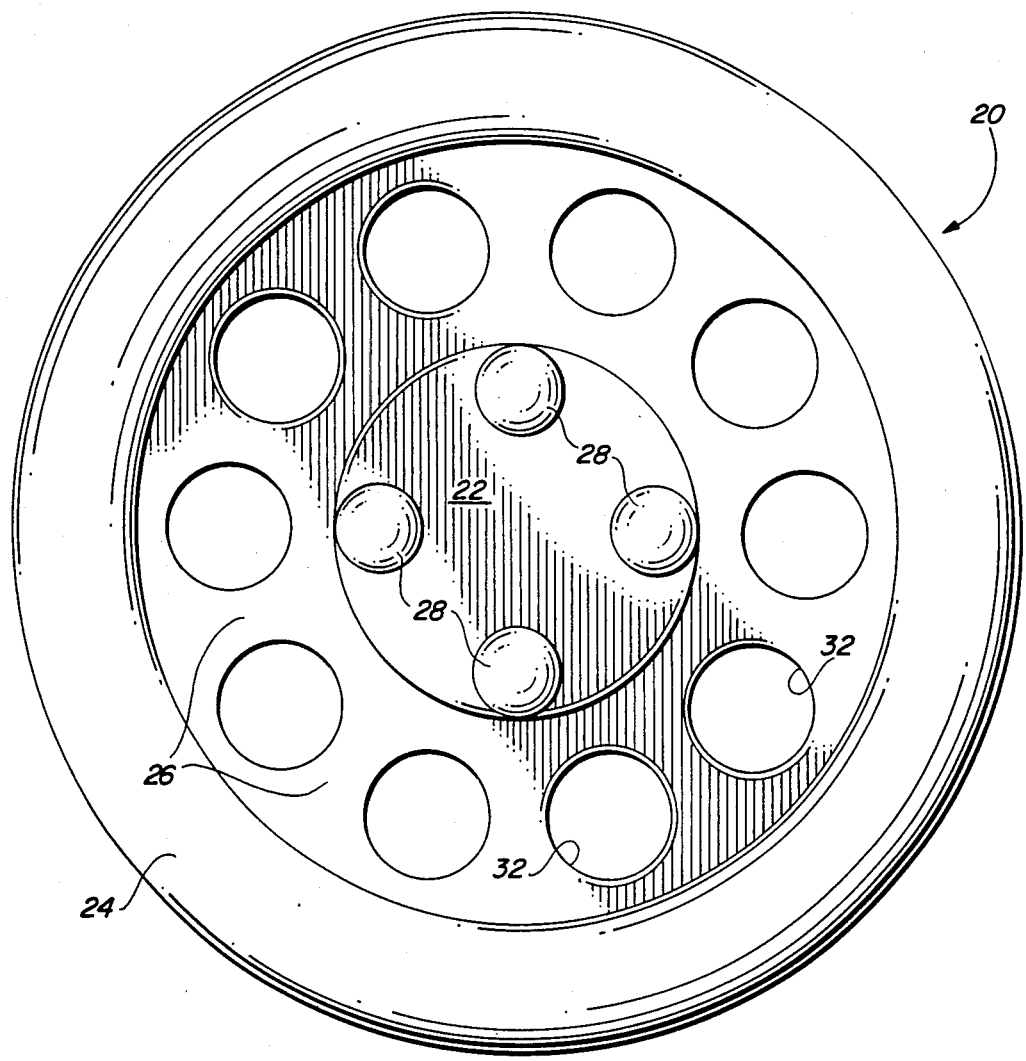
FIG. 3 is a plan view of the bottom side of the valve shown in FIGS. 1 and 2.

Referring now to FIGS. 1-3, a valve 20 is illustrated which is constructed according to the teachings of the present invention. Basically, the valve 20 consists of three elements, the first of which is a rigid valve disk 22 which includes sealing means and which functions as the actual valve element. The second element of the valve 20 is a static seal ring 24 which acts both as a seal between upper and lower housing elements (not shown in FIGS. 1 and 2) and as a rigid support structure from which the valve disk 22 may be suspended. The third element is a thin support web 26 extending between the inner diameter of the static seal ring 24 and the outer diamerter of the valve disk 22. The support web is used both to support the valve disk 22 in the proper operating location within housing elements and to bias the valve disk 22 in a closed position which a preselected force in the proper direction may be overcome to open the valve 20.

The valve 20 is quite small, typically having a diameter of approximately 0.20–0.75 inches. For purposes of an example used to illustrate the preferred embodiment, a valve 20 will be described herein which has a diameter of 0.33 inches. It will be recognized by those skilled in the art that the teachings of the present invention are equally applicable to valves of differing sizes for use in such medical devices.

The valve disk 22 is relatively thick to prevent it from exhibiting a significant amount of flexure, particularly under situations when a high pressure in the direction opposite flow would otherwise tend to cause a deflection. It will be appreciated by those skilled in the art that infusion pumps have a relatively small pump displacement, and therefore even a small amount of flexure by the valve disk 22 during pumping would result in both a significant reduction in volumetric efficiency and in an imprecise amount of medication being delivered, making the pump unsuitable for the medical use for which it is intended. In the example used herein, the valve disk 22 has a diameter of 0.12 inches, and a thickness of 0.025 inches.

As used throughout this disclosure, the term "top" of the valve 20 shall be used to mean the side from which fluid originates, and the term "bottom" of the valve 20 shall mean the side of the valve 20 from which fluid exits as it passes through the valve 20. The side shown in the plan view of FIG. 1 is the top side of the valve 20, and the side shown in the plan view of FIG. 3 is the bottom side of the valve 20. The top side is shown in FIG. 2 at the top of the figure when viewed in the conventional manner, and the bottom is likewise shown at the bottom of the figure.

The valve 20 has on the bottom side thereof four protruding circular ridges or bumps 28, as shown best in FIG. 3. The four bumps 28 are mounted around and extend from the periphery of the valve disk 22 on the bottom side of the valve disk 22. They are evenly distributed around the bottom of the valve disk 22, at positions separated by ninety degrees. The purpose of the bumps 28 is to prevent the valve disk 22 from bottoming out and closing off the fluid path, as will be discussed later in this specification.

The valve disk 22 has on the top side of the valve 20 from which fluid originates a dynamic sealing ridge 30, shown best in FIGS. 1 and 2. The dynamic sealing ridge 30 is cylindrical and extends upwardly from from the outside edge of the valve disk 22. The dynamic sealing ridge 30 extends 0.01 inches above the surface of the valve disk 22 in the exemplar valve, and has a rounded top surface for enhanced sealing characteristics.

It of course will be appreciated by those skilled in the art that the shape of the valve disk 22 may be other than circular as shown herein. Additionally, the configurations of the bumps 28 or the sealing ridge 30 may be different, the designs discussed above merely representing the preferred embodiment.

The static seal ring 24 is located concentrically around the valve disk 22, and functions to support and locate the valve disk 22 in position. The static seal ring also functions as a gasket or an O-ring to seal the space between the two housing portions, as will become more evident below in conjunction with the discussion of FIGS. 3 and 4. It is important to note that while the cross-sectional configuration of the static seal ring 24 shown in FIG. 2 is the preferred embodiment, other configurations are possible. The static seal ring must present both a conveniently sealing design and a structurally sound base from which the valve disk 22 is supported. The U-shaped cross-section static seal ring 24 shown in FIG. 2 accomplishes both objectives admirably.

The thin support web 26 is used to support the valve disk 22 from the static seal ring 24, with the valve disk being capable of movement in essentially one direction only—up and down. Since the entire valve 20 is constructed of elastomeric material, it will be appreciated that the web 26 will tend to bias the valve disk 22 in the position shown in FIG. 2 when no outside forces are applied to the valve 20. In this position the top surface of the static seal ring 24 and the support web 26 are entirely planar, with the dynamic sealing ridge and a portion of the valve disk 22 protruding above this plane.

By manufacturing the valve 20 with uniform dimensions, the force, and hence the fluid pressure, required to displace the valve disk 22 will be highly repeatable. Since the fluid pressure required to supply this force is to be very small, i.e. on the order of 0.1 PSI, it will be appreciated that the support web must be very thin.

An additional factor is the use in the valve 20 of the present invention of a plurality of apertures 32 through the support web, the apertures 32 being arranged uniformly around the circumference of the valve disk 22. In the preferred embodiment shown, there are 10 apertures 32 in the support web 26, each aperture 32 having a diameter of 0.042 inches. Since the outer diameter of the support web 26 where it is connected to the static seal ring 24 is 0.25 inches in the preferred embodiment, the apertures remove a substantial portion of the support web 26, thereby diminishing the force and the fluid pressure necessary to displace the valve disk. The practical effect of the apertures 32 is that the support web 26 may be made thicker, which in the manufacturing sense makes the valve 20 both easier and more inexpensive to fabricate. Of course, the apertures 32 also serve the purpose of allowing the passage therethrough of fluid entering the valve 20 when the valve disk 22 is open.

It will be appreciated that the valve 20 may be manufactured by molding procedures well known in the art, such as but not limited to injection molding or transfer molding, with the valve 20 illustrated being manufactured in one piece construction. The valve is typically molded of a medical grade elastomer such as silicone rubber. A critical design criteria is the hardness of the elastomer, which is a compromise between conflicting design considerations.

The static seal ring 24 must have a low stress relaxation characteristic in order to form a good seal after an extended shelf life. A durometer hardness of 30–70 on the Shore A scale encompasses the outer limits on hardness of the material used for the valve 20, with the hardness in the preferred embodiment being between 40 and 50 on the Shore A scale.

Figure 4:
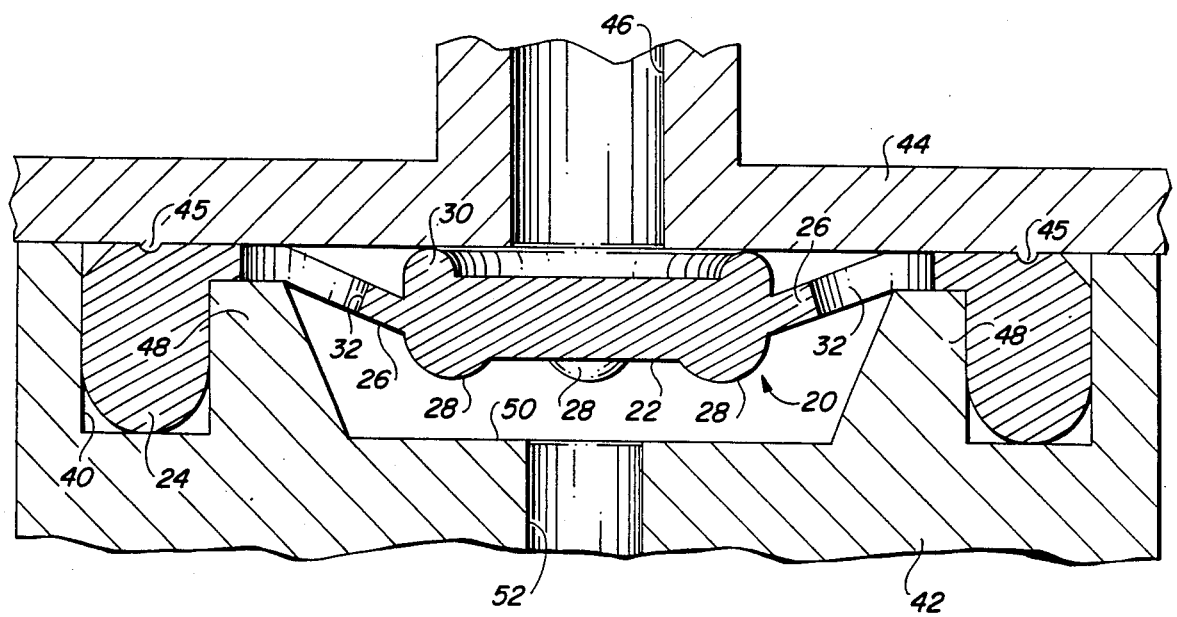
FIG. 4 is a view of the valve shown in FIGS. 1-3 installed between first and second housing portions, with the valve in the closed position.

With the construction of the valve 20 being accomplished in sufficient detail, the installation of a valve 20 in the two housing portions is illustrated in FIG. 4. The static seal ring 24 of the valve 20 is inserted into a circular seal retaining slot 40 in a lower housing portion 42. The retaining slot 40 is of sufficient depth to accept the portion of the static seal ring 24 in a sealing manner.

An upper housing portion 44 is then lowered into position over the valve 20 and the lower housing portion 44, and secured in position by any of a number of techniques well known in the art, such as by snapping the upper housing portion 44 onto the lower housing portion 42. The installation of the upper housing portion 44 onto the lower housing portion will also compress the static seal ring 24 to form an excellent seal between the upper housing portion 44 and the lower housing portion 42 at the location of the static seal ring 24.

Also illustrated in FIG. 4 is an optional circular protruding ridge 45, which may be formed on the upper housing portion in a manner whereby the circular protruding ridge 45 will be located over a central portion of the top of the static seal ring 24 to ensure an even better seal. It should be noted that with the possible exception of the protruding ridge 45, the side of the upper housing portion 44 facing the valve 20 is flat, thereby accomplishing one of the objects of the present invention.

Centrally located above the valve disk 22 and within the dynamic sealing ridge 30 is an inlet aperture 46, through which fluid may be admitted to the valve. Since the side of the upper housing portion 44 facing the valve 20 is flat, it will be appreciated that the installation of the upper housing portion 44 over the valve 20 causes the dynamic sealing ridge 30 and the valve disk 22 to be moved downwardly, thereby prestressing the support web 26 and preloading the valve 20 in a closed position. The pressure differential must reach a threshold value in order to open the valve 20 by forcing the valve disk 22 and the dynamic sealing ridge 30 away from the upper housing portion 44. In the preferred embodiment described herein, the preload requires only a minimal break pressure to open the valve, typically about 0.1 PSI. It is important that the material of the valve 20 have characteristics such that this prestressing of the valve 20 not result in stress relaxation by the material, as discussed above.

It will be noted that the design of the valve 20 on the inlet side requires and allows only a very small volume of fluid to be stored therein in the cavity formed between the top of the valve disk 22, the interior of the dynamic sealing ridge 30, and the side of the upper housing portion 44 facing the valve 20. This is important to minimize the volume contained within this area on the inlet side of the valve 20 when the valve 20 is used as the valve 18B at the outlet side of the pump 14 shown in FIG. 6.

The design of the valve 20 also allows this volume to be minimized on the outlet side of the valve 20. Referring again to FIG. 4, a web support 48 is integrally fashioned in the lower housing portion radially inside the seal retaining slot 40, with the web support forming the interior side of the seal retaining slot 40. As its name implies, the web support also extends inwardly from the seal retaining slot slightly to support a small portion of the support web 26, in the process slightly increasing the force required to open the valve 20.

An additional function of the web support 48 is to minimize the volume in the chamber outside of the dynamic sealing ridge 30 and between the upper housing portion 44 and the lower housing portion 42, this chamber being on the outlet side of the valve 20. A valve chamber floor 50 is located beneath the valve disk 22, and an outlet aperture 52 is located in the valve chamber floor 50. The web support may be larger than depicted in FIG. 4, so long as it does not obstruct the valve disk 22 or the flow of fluid through the apertures 32 and around the valve disk 22. The web support 48 therefore minimizes the volume contained on the outlet side of the valve 20, which is important when the valve 20 is used as the 18A at the inlet side of the pump 14 shown in FIG. 6.

Since the force needed to open the valve 20 is very small, it is important to prevent the situation where a high inlet pressure could force the valve disk 22 to the valve chamber floor 50, thereby obstructing the outlet aperture 52 and the flow through the valve 20. The four protruding circular bumps 28, discussed above in conjunction with FIGS. 2 and 3, extend away from the bottom side of the valve disk 22 to prevent the valve disk 22 from blocking the outlet aperture 52 even under the conditions described above. The spaces between the bumps 28 and the facing surfaces of the valve disk 22 and the floor 50 of the lower housing portion 42 thereby provide a fluid path even when the valve disk 22 is forced downwardly by excessive force.

Figure 7:
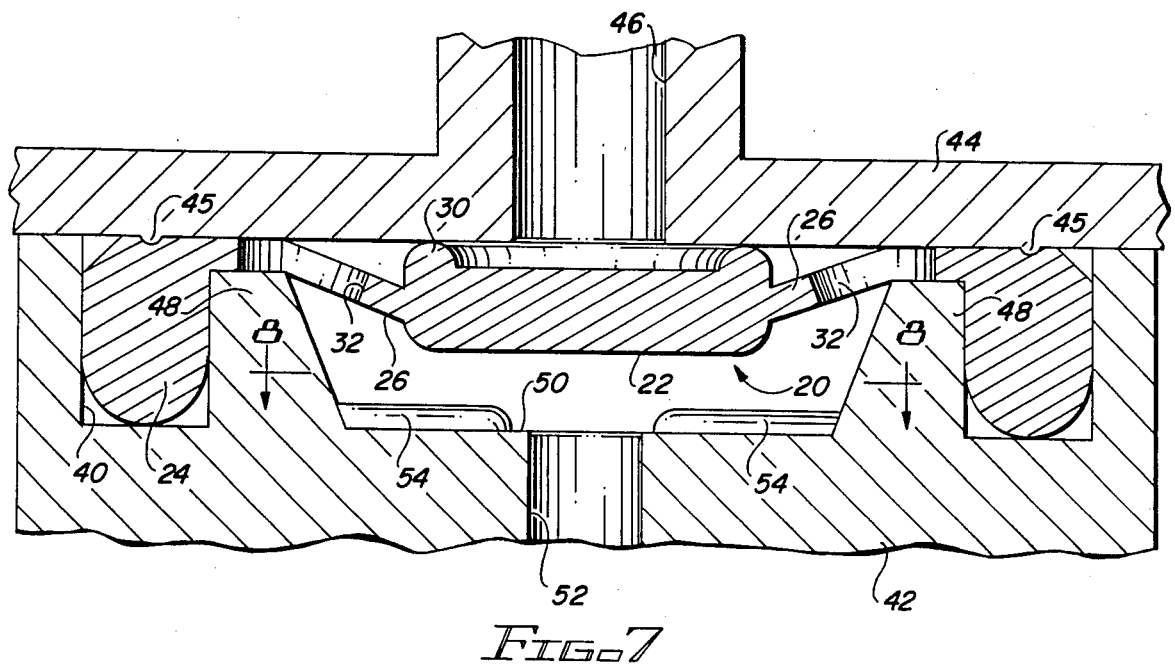
FIG. 7 is a cross-sectional view of an alternate embodiment using valve stop ribs on the floor of the lower housing portion to prevent overtravel by the valve disk rather than using bumps on the bottom side of the valve disk.
Figure 8:
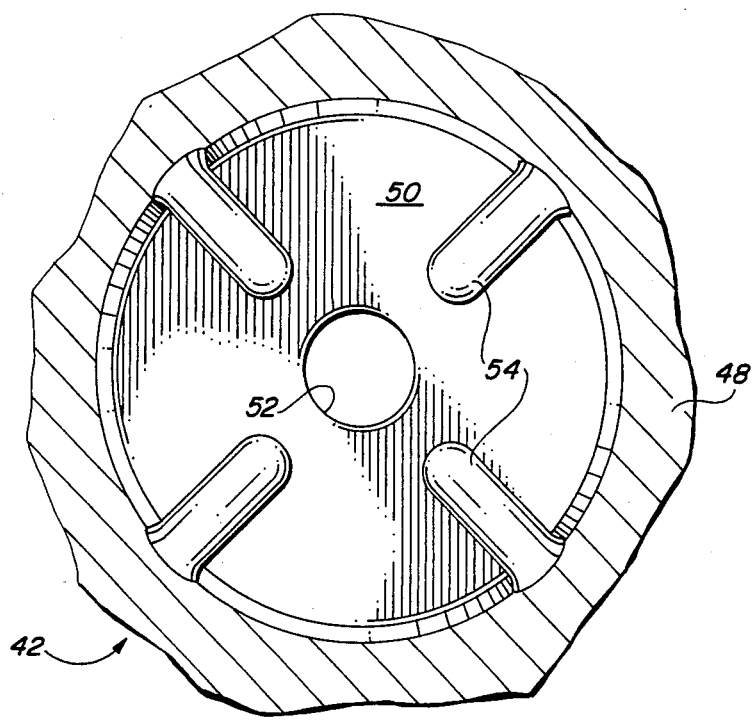
FIG. 8 is a cross-sectional view of the top side of the lower housing portion shown in FIG. 7.

Alternatively, rather than having the bumps 28 molded into the bottom of the valve disk 22, apparatus for preventing the valve disk 22 from blocking the outlet aperture 52 under the conditions described above could be located on the floor 50 of the lower housing portion 42. The bottom side of the valve disk 22 would not have the protruding bumps 28 but rather would be essentially flat with a rounded bottom edge. As shown in FIGS. 7 and 8, one or more valve stop ribs 54 which protrude from the floor 50 of the lower support portion 42 prevent the valve disk 22 from bottoming out and obstructing the outlet aperture 52. The space between the valve stop ribs 54 would thereby provide a fluid path when the valve disk 22 is against the valve stop ribs 54.

Figure 5:
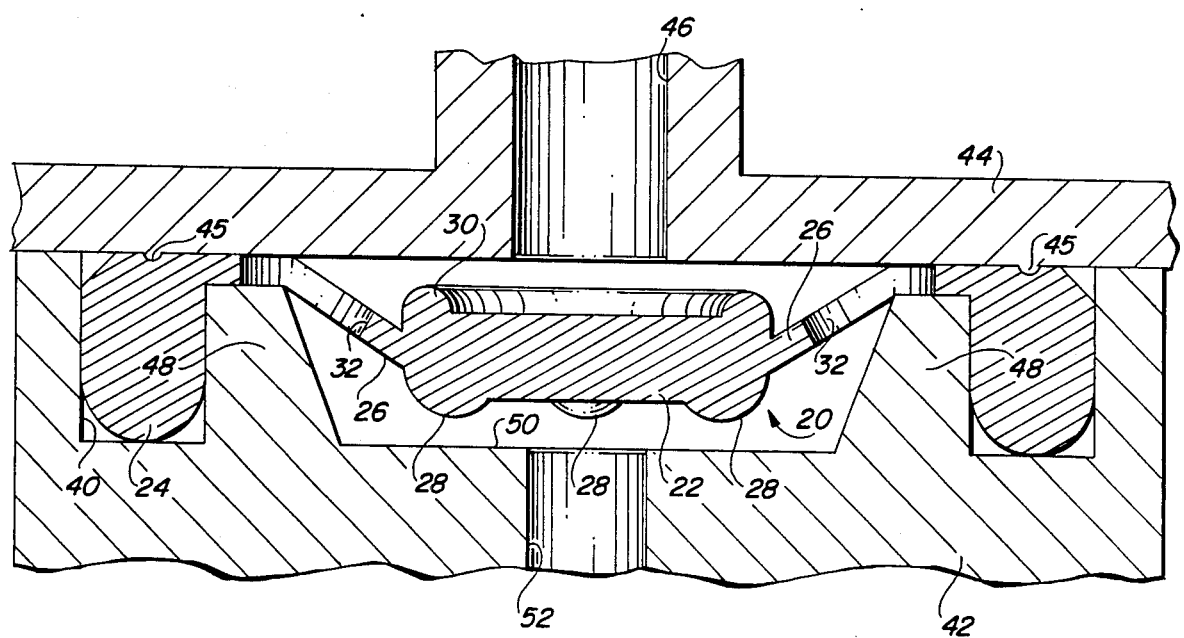
FIG. 5 is a view of the valve of FIGS. 1-3 installed as shown in FIG. 4 between the first and second housing portions, with the valve in an open position.

The spring action of the support web 26 will maintain the dynamic sealing ridge 30 of the valve disk 26 against the upper housing portion 44 as shown in FIG. 4 when there is no fluid pressure, when the pressure differential across the valve is less than the break pressure, and when the pressure on the outlet side of the valve 20 is greater than the pressure on the inlet side of the valve 20. When the pressure on the inlet side of the valve 20 is greater than the pressure on the outlet side of the valve 20 by a value at least that of the break pressure, the valve 20 will open as shown in FIG. 5, allowing fluid to flow in the inlet aperture 46, around the dynamic sealing ridge 30, through the apertures 32 in the support web 26, and out the outlet aperture 52.

The support web 26 will act to return the valve 20 to a closed position when the pressure across the valve 20 drops below the break pressure. The valve 20 is highly resistant to reverse flow since the valve disk 22 is relatively thick to prevent substantial deflection therein, thereby maintaining the dynamic sealing ridge 30 tightly against the upper housing portion 44.

It is therefore apparent that the design of the valve 20 to have a desired break pressure is determined by three factors. First, the thicker the support web, the higher the spring rate and the greater the break pressure of the valve 20. Secondly, the apertures 32 in the support web act to reduce the spring rate and the break pressure of the valve 20 as the number and size of the apertures increase. Finally, the height by which the dynamic sealing ridge 30 projects above the support web 26 provides an offset which determines the preload of the valve disk 22 and the dynamic sealing ridge 30 against the upper housing portion 44.

The valve 20 of the present invention is highly precise, and may be economically manufactured. It is suitable for use in medical devices since it is precise, has good shelf and operating lives, and is made of medical grade materials. The valve 20 has a very small break pressure, yet it seals tightly when this break pressure is not met. It may be used in conjunction with a flat top surface (the upper housing portion 44), thereby making construction of a more economical infusion pump possible and making practical an inexpensive disposable pump with positive valve operation. The present invention thereby represents a valuable and highly desirable improvement in the art, while affording no relative disadvantages.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A one-way precision valve for medical applications, said valve for mounting between an upper housing portion having an essentially flat surface with an inlet aperture therein and a lower housing portion having an outlet portion therein, said valve being of one-piece manufacture and comprising:

a rigid circular valve disk, wherein said valve disk is so arranged and configured as to be of a thickness sufficiently substantial to prevent said valve disk from exhibiting a significant amount of flexure even under high reverse pressure;

a cylindrical dynamic sealing ridge protruding from the top side of said rigid circular valve disk, said dynamic sealing ridge for providing a sealing contact with said flat surface of said upper housing portion around said inlet aperture when said valve disk is urged toward said upper housing portion;

a static seal ring for installation between said upper and lower housing portions in sealing fashion, said static seal ring being located circumferentially around and spaced away from said valve disk; and a relatively thin support web extending between said static seal ring and said valve disk for supporting said valve disk from said static seal ring, said support web being flat when in an unbiased position, said support web supporting said dynamic sealing ridge on said valve disk in position around said inlet aperture, said dynamic sealing ridge being located above the surface of said support web, said support web being elastomeric and functioning to bias said valve disk toward said upper housing portion to maintain said dynamic sealing ridge against said upper housing portion around said inlet aperture in sealing fashion until and unless a predetermined forward pressure drop exists across said valve, said support web having disposed therein a plurality of apertures to allow the passage of fluid therethrough.

2. A valve as defined in claim 1, wherein said valve is manufactured of an elastomeric material of medical grade.

3. A valve as defined in claim 2, wherein said elastomeric material is silicone rubber having a durometer hardness of between 30 and 70 on the Shore A scale.

4. A valve as defined in claim 3, wherein said elastomeric material is silicone rubber having a durometer hardness of between 40 and 50 on the Shore A scale.

5. A valve as defined in claim 1, wherein said dynamic sealing ridge has a rounded top surface to enhance the sealing characteristics thereof.

6. A valve as defined in claim 1, wherein said dynamic sealing ridge extends above the top side of said valve disk by approximately 0.01 inches.

7. A valve as defined in claim 1, wherein said support web extends from a location substantially at the top of said static seal ring to said valve disk at a height not exceeding the top of said valve disk, said dynamic sealing ridge thereby extending above said support web and functioning to bias said valve disk downward when said essentially flat surface of said upper housing portion contacts the top of said static seal ring.

8. A valve as defined in claim 7, wherein said valve is biased in a closed position until the forward pressure drop across said valve is at least 0.1 PSI.

9. A valve as defined in claim 1, wherein said valve is so arranged and configured as to minimize the volume of fluid which may be contained around said valve and between said upper and lower support portions.

10. A valve as defined in claim 1, wherein said static seal ring is relatively rigid to thereby support said valve disk.

11. A valve as defined in claim 1, wherein said support web has ten apertures disposed therein, said apertures being arranged about said valve disk.

12. A valve as defined in claim 1, additionally comprising:

means for reducing the amount of biasing force caused by prestressing of said support web, said reducing means being provided by the relative arrangement and configuration of said apertures and said support web.

13. A valve as defined in claim 1, additionally comprising:

means for supporting a portion of said support web adjacent said static seal ring, said supporting means including a web support portion of said lower housing portion.

14. A valve as defined in claim 1, wherein said valve has an outer diameter of between 0.2 and 0.75 inches.

15. A valve as defined in claim 1, additionally comprising:

means for preventing a large forward pressure across said valve from causing said valve disk to block or obstruct said outlet aperture in said lower housing portion.

16. A valve as defined in claim 15, wherein said preventing means comprises:

at lease one bump extending below the bottom surface of said valve disk to prevent said bottom surface of said valve disk from obstructing said outlet aperture.

17. A passive one way valve for use in the pump of a medication infusion system, said valve being installed between a lower housing portion and an upper housing portion, said upper housing portion having an inlet aperture located in an essentially flat surface facing said valve, said lower housing portion having an outlet aperture located therein, said valve being of one-piece manufacture and comprising:

a circular static seal ring located in a slot in said lower housing portion concentrically around said inlet aperture in said upper housing portion, said static sealing ring providing a seal between said upper and lower housing portions, said static seal ring being relatively rigid to thereby support said valve;

a rigid circular valve disk having on one side a protruding cylindrical dynamic sealing ridge, wherein said valve disk is so arranged and configured as to be of a thickness sufficiently substantial to prevent said valve disk from exhibiting a significant amount of flexure even under high reverse pressure, said protruding cylindrical dynamic sealing ridge comprising the valve element of said valve;

a thin support web extending between the inner diameter of said static seal ring and the outer diameter of said valve disk, said support web being flat when in an unbiased position, said support web for supporting said valve disk from said static seal ring and biasing said dynamic sealing ridge of said valve in a closed position against said upper housing portion and around said inlet aperture, said dynamic sealing ridge being located above the surface of said support web, said support web having a plurality of holes therein to allow fluid passage therethrough; and a plurality of bumps extending below the bottom side of said valve disk to prevent said bottom surface of said valve disk from obstructing said outlet aperture, said plurality of bumps having spaces therebetween through which fluid may flow even when said valve disk in subject to high forward pressure.

* * * * *